(12) United States Patent
Oxford

(10) Patent No.: US 10,488,233 B2
(45) Date of Patent: Nov. 26, 2019

(54) SYSTEMS AND METHODS FOR DETECTING OIL IN A FLUID MIXTURE

(71) Applicant: Integrated Advantage Group, L.P., Amarillo, TX (US)

(72) Inventor: Derek Oxford, Apollo Beach, FL (US)

(73) Assignee: Integrated Advantage Group, L.P., Amarillo, TX (US)

( * ) Notice: Subject to any disclaimer, the term of this patent is extended or adjusted under 35 U.S.C. 154(b) by 428 days.

(21) Appl. No.: 15/462,993

(22) Filed: Mar. 20, 2017

(65) Prior Publication Data

US 2018/0266858 A1 Sep. 20, 2018

(51) Int. Cl.
| | |
|---|---|
| G01F 1/36 | (2006.01) |
| G01F 1/88 | (2006.01) |
| G01F 1/74 | (2006.01) |
| G01N 33/28 | (2006.01) |

(52) U.S. Cl.
CPC ............... *G01F 1/363* (2013.01); *G01F 1/74* (2013.01); *G01F 1/88* (2013.01); *G01N 33/2823* (2013.01)

(58) Field of Classification Search
CPC .. G01F 1/363; G01F 1/74; G01F 1/88; G01N 33/2823
See application file for complete search history.

(56) References Cited

U.S. PATENT DOCUMENTS

| | | | | | |
|---|---|---|---|---|---|
| 4,623,389 | A | * | 11/1986 | Donley | ............. H01B 1/16 106/1.14 |
| 4,776,210 | A | * | 10/1988 | Baillie | ........... E21B 49/086 73/61.47 |
| 4,872,351 | A | * | 10/1989 | Ruesch | ............. G01F 1/74 73/861.04 |
| 5,070,725 | A | * | 12/1991 | Cox | ........... E21B 47/102 73/61.44 |
| 5,857,522 | A | * | 1/1999 | Bradfield | ............ E21B 21/06 166/267 |

* cited by examiner

*Primary Examiner* — Mischita L Henson
(74) *Attorney, Agent, or Firm* — Clayton, McKay & Bailey, PC

(57) ABSTRACT

An oil-detection unit is provided that can include a reference cell, a flow meter that measures the flow rate of the fluid mixture through the reference cell, and a processor. The processor can receive signals from each of the sensors, as well as from the flow meter. Using these signals, the processor can determine whether the fluid mixture contains at least a threshold amount of oil. To make this determination, the processor can establish a baseline range of values received from the sensors and compare that output to the established baseline range. The processor can recalculate the baseline range of values continuously or after a predetermined period of time. Based on a determination that the fluid mixture contains at least the threshold amount of oil, the processor can initiate an alarm.

20 Claims, 4 Drawing Sheets

SYSTEMS AND METHODS FOR DETECTING OIL IN A FLUID MIXTURE

DESCRIPTION OF THE EMBODIMENTS

Field of the Embodiments

The embodiments herein relate generally to detecting the presence of oil, and, more specifically, to systems and methods for detecting oil in a fluid mixture.

Backgound

Some oil- and gas-extraction techniques, such as hydraulic fracturing, produce a fluid mixture from the earth that can include oil, gas, water, fracking chemicals, and other particulates. The oil and gas must be separated from the water, chemicals, and particulates before being transported or sold. As a result, a more effective process for separating the oil and gas from the fluid mixture will result in higher profit margins.

Typically, a three-phase separator is used onsite at oil wells to separate oil and gas from a fluid mixture. A three-phase separator provides several primary functions, including removing oil from gas, removing gas from oil, and separating water from oil. Separators typically utilize chemicals to assist in separating water from oil. For example, a dosing pump can be placed upstream from a three-phase separator to dose the fluid mixture with chemicals that assist in the separation. The oil and gas extracted by the separator can be transported and sold.

The leftover fluid from the separator can still include oil and gas. Typically, this fluid is processed by one or more additional oil-water separators, such as a gun-barrel separator, skimmer, or both. The extracted oil or gas can then be sold, while the remaining fluid is rejected as a waste product.

However, even after processing fluid through a three-phase separator, gun barrel separator, and skimmer, the leftover fluid mixture can still contain oil. This is especially true as the composition of the incoming gas and oil mixture changes, rendering the chemical dosing inaccurate. Additionally, any failure in the separation processes can leave oil in the resulting fluid mixture. This oil is not captured, lowering profit margins and increasing environmental waste. By the time an oil-well operator learns of a malfunction or miscalibration in the separation process, large amounts of oil will already have been lost in the waste fluid.

As a result, a need exists for real-time detection of oil in a fluid mixture. In particular, a need exists for a systems and methods that detect the presence of oil in a fluid mixture and alert the appropriate oil-field personnel.

SUMMARY

Embodiments described herein include a reference cell for detecting the presence of oil in a fluid mixture, an oil-detection unit, and a non-transitory, computer-readable medium containing instructions that, when executed by a processor, performs stages for detecting the presence of oil in a fluid mixture.

The reference cell can include multiple ports coupled to the passageway. The ports can be used to house multiple sensors, with each sensor positioned at least partially within one of the ports. Each of the sensors can produce a signal indicative of the excitation of the fluid mixture flowing through the reference cell. Excitation can include resistivity, conductivity, or any other measure of excitation in the fluid mixture.

The inner surface of the passageway can include spiral grooves, or "rifling," that causes the fluid mixture to flow in a spiraling manner. The multiple ports coupled to the passageway can be oriented such that their respective central axes form at least a 10-degree angle, relative to one another, when viewed from a perspective aligned with the overall direction of fluid flow through the reference cell. The location of the ports, combined with the spiral grooves in the passageway, can ensure accurate measurements of the fluid mixture.

In another example, an oil-detection unit can include a reference cell, a flow meter that measures the flow rate of the fluid mixture through the reference cell, and a processor. The processor can receive signals from each of the sensors, as well as from the flow meter. Using these signals, the processor can determine whether the fluid mixture contains at least a threshold amount of oil. The processor can determine whether the fluid mixture contains at least a threshold amount of oil by establishing a baseline range of values received from the sensors, and comparing the output from the sensors to the established baseline range. The processor can recalculate the baseline range of values continuously or after a predetermined period of time. Based on a determination that the fluid mixture contains at least the threshold amount of oil, the processor can initiate an alarm. The alarm can include sending an electronic notification, such as a SMS, MMS, email, or instant message, to a user or administrator.

In yet another example, a non-transitory, computer-readable medium is provided. The computer-readable medium can contain instructions that, when executed by a processor, performs stages for detecting the presence of oil a fluid mixture. The stages can include, for example, receiving information from multiple sensors. The information can indicate an excitation level of the fluid mixture. Another stage can include determining a baseline range of values based on the received information. The baseline range of values can represent a fluid mixture having less than a threshold proportion of oil. Another stage can include monitoring the information received from the sensors to determine whether that information corresponds to values outside of the determined baseline range of values. In response to one or more of the sensors providing information corresponding to values outside of the baseline range, the processor can initiate an alarm sequence. This can include, for example, sending a notification to a user or administrator.

Determining the baseline range of values can include recalculating the baseline range of values continuously or after a predetermined period of time. When an alarm sequence is initiated, the processor can stop recalculating the baseline range of values to avoid infecting the measurements with inaccurate values. During an alarm sequence, the processor can continue to monitor the information received from the sensors. When that information corresponds to values that are within the baseline range, the alarm sequence can be abated. Once the alarm sequence is abated, the processor can resume the continuous or periodic calculation of a baseline range of values.

Both the foregoing general description and the following detailed description are exemplary and explanatory only and are not intended to restrict the scope of the invention as claimed.

BRIEF DESCRIPTION OF THE DRAWINGS

The accompanying drawings, which are incorporated in and constitute a part of this disclosure, illustrate various embodiments and aspects of the present invention. In the drawings.

DETAILED DESCRIPTION

Reference will now be made in detail to the present exemplary embodiments, including examples illustrated in the accompanying drawings. Wherever possible, the same reference numbers will be used throughout the drawings to refer to the same or like parts.

Figure 1:
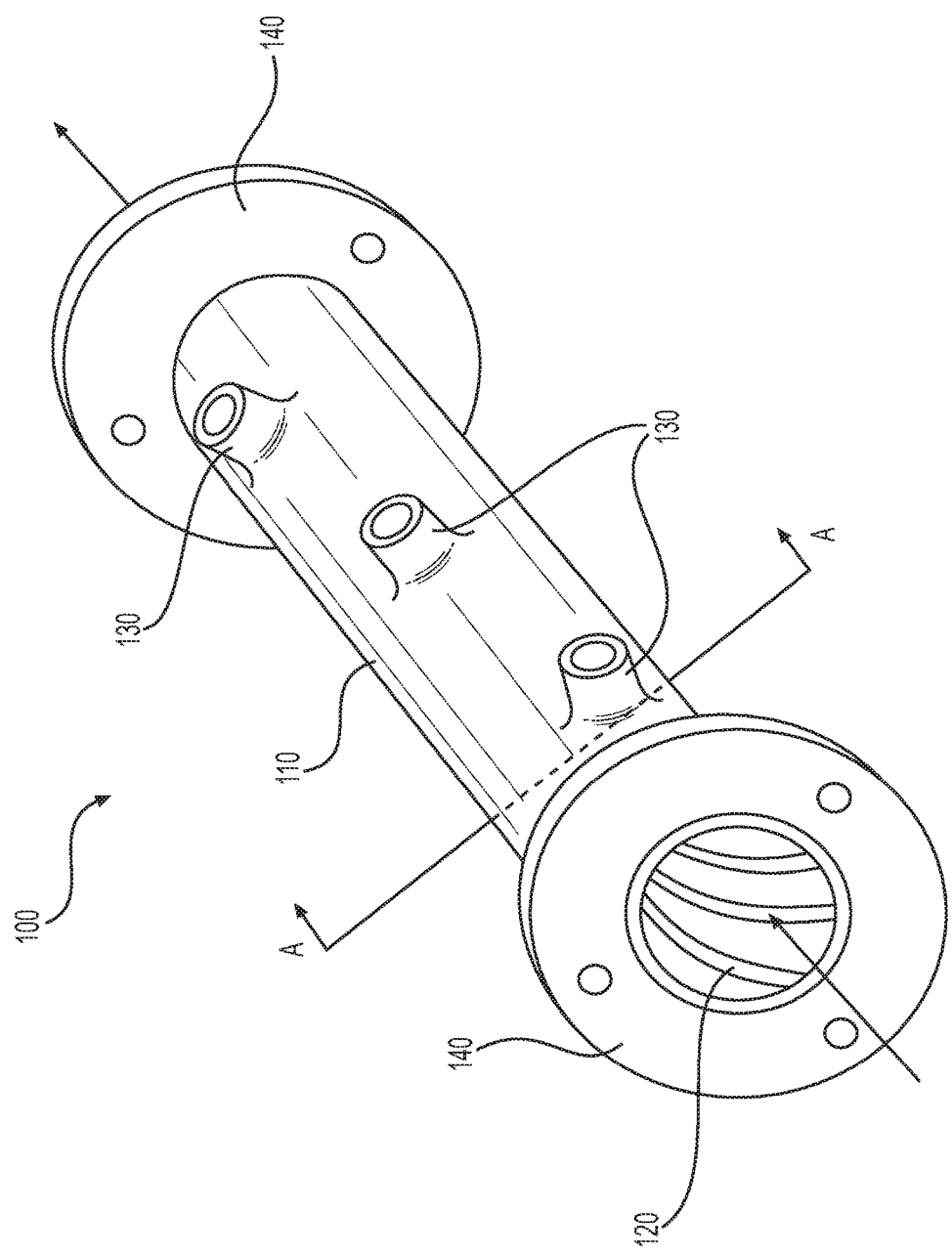
FIG. 1 is an illustration of an example embodiment of a reference cell having three ports for sensors.

FIG. 1 provides an illustration of an example reference cell 100 that can be used in an oil-detection unit. The reference cell 100 includes a passageway 110 for channeling a fluid mixture. In the illustration of FIG. 1, the fluid mixture flows in the direction of the arrows aligned axially with the length of the passageway 110. As used herein, "fluid mixture" can include a mixture of any type of fluid, including water, oil, gas, and any chemicals used in the hydraulic fracturing process, for example. The passageway 110 can be made from a durable material such as copper or steel. In some applications, the passageway 110 can be made from a polymer material.

The flow of the fluid mixture can be altered by spiral grooves 120 located on the inner surface of the passageway 110. The spiral grooves 120 can include one or more grooves that run the length of the passageway 110 in a spiraling manner. The shape and depth of the spiral grooves 120 can vary based on various factors. Generally, deeper and wider grooves 120 will have a greater influence on the flow of the fluid mixture through the passageway 110. With a sufficient flow rate, spiral grooves 120 can cause the fluid to flow in a spiraling direction, such that the mixture is not allowed to separate. When the flow rate is lower, the spiral grooves 120 can still induce turbulence that causes blending of the various fluids in the fluid mixture. The number, width, and depth of the spiral grooves 120 can be matched to the anticipated flow rate of the fluid mixture, such that the mixture is rotated around the entire inner surface of the passageway 110.

Various ports 130 can be formed into the surface of the passageway 110. The ports 130 can be used to house sensors (discussed in more detail with respect to FIG. 2) that measure aspects of the fluid mixture as it flows through the reference cell 100. In some examples, multiple ports 130 are included in the reference cell 100. Using multiple ports 130 increases accuracy and allows for a method to recognize malfunctioning sensors. Multiple ports 130 can also be used to cover a greater proportion of the fluid flow through the passageway 110, such that the sensors are measuring the fluid mixture in multiple locations. For example, three ports 130 can be used. However, there is no limit to the number of ports 130 that can be included on the reference cell 100. A greater number of ports 130 increases accuracy but also increases complexity and cost. The positioning of the ports 130 is described in more detail with respect to FIG. 2.

The reference cell 100 can also include flanges 140 at either end of the passageway 110. The flanges 140 can be used, for example, to connect the reference cell 100 to other components of the oil-detection unit. In the example of FIG. 1, the reference cell 100 includes flanges 140 at both ends of the passageway 110. These example flanges each have three apertures for receiving fasteners that pair the flange 140 to an accompanying flange of another oil-detection-unit component, such as a pipe or valve. The flanges 140 can be made from a durable material such as copper or steel, and can be welded to the passageway 110 for optimum strength. In some applications, the flanges 140 can be made from a polymer material and attached to the passageway 110 using an epoxy, for example.

A cross-sectional line, A-A, is shown drawn through the center of the passageway 110 at a location along the passageway 110 between a flange 140 and a port 130. The view from this cross-sectional line is shown in FIG. 2.

Figure 2:
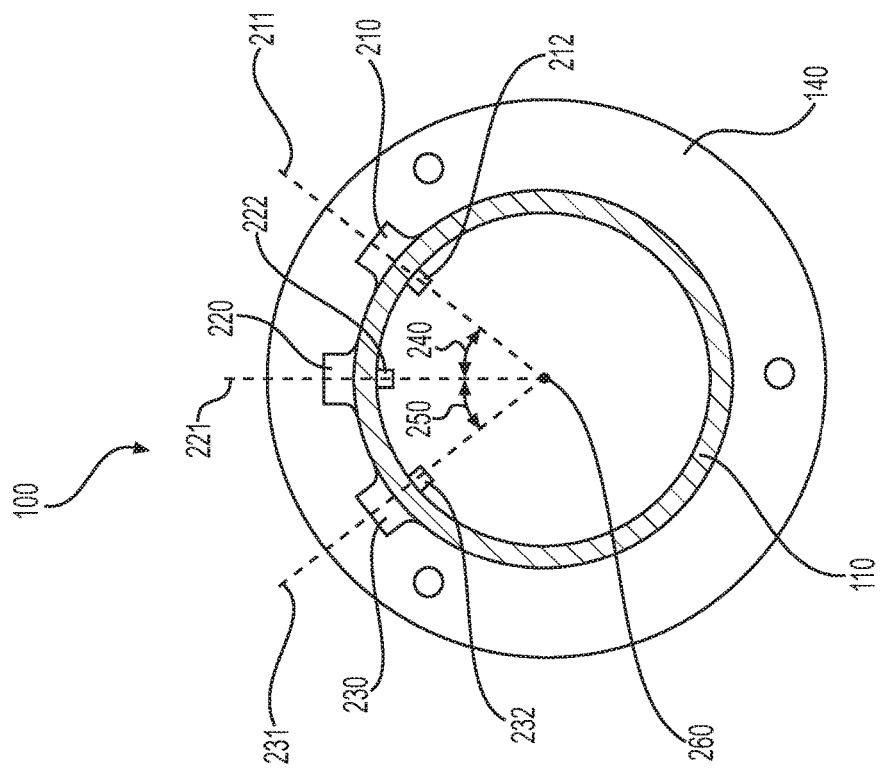
FIG. 2 is a cross-sectional view of the example embodiment of FIG. 1, viewed from cross section A-A.

FIG. 2 provides a cross-sectional view of a reference cell 100 having three ports 210, 220, 230 arranged at locations along the passageway 110. In the example shown in FIG. 2, the first port 210 is closest to the cross-sectional viewpoint, while the third port 230 is furthest. The second port 220 is located between the first port 210 and third port 230 along the passageway 110. This aligns with the drawing shown in FIG. 1. This orientation is merely exemplary, and others can be used.

Each of the ports 210, 220, 230 can be associated with a sensor 212, 222, 232, respectively. The sensors 212, 222, 232 can be housed within each port 210, 220, 230 such that the sensors 212, 222, 232 contact the fluid mixture as it flows through the passageway 110. Any type of sensor can be used. For example, the sensors can detect changes in pH levels, viscosity, optical transparency, or electrical resistivity or conductivity, among other things.

As shown in FIG. 2, each port 210, 220, 230 is associated with a central axis 211, 221, 231, respectively. The ports 210, 220, 230 are aligned such that each central axis 211, 221, 231 passes through the center point 260 of the passageway 110. The center point 260, as viewed from cross section A-A, can also be described as a longitudinal axis of the passageway 110 aligned with the overall direction of fluid flow through the reference cell 100. The fluid mixture can flow in a spiral or turbulent manner, but the overall direction of fluid flow aligns with the passageway 110, and similarly, with the central axis of the passageway 110 that coincides with center point 260.

When viewed from cross section A-A, the central axes 211, 221, 231 of the ports 210, 220, 230 can form angles relative to one another. For example, in FIG. 2, an angle 240 is formed between the central axes 211, 221 of the first port 210 and second port 220, respectively. Similarly, another angle 250 is formed between the central axes 221, 231 of the second port 220 and third port 230, respectively. In one example, each of these angles 240, 250 can be at least 10 degrees. In another example, each of the angles 240, 250 can be at least 20 degrees. In other examples, each of the angles 240, 250 can be at least 30, 45, 60, or 90 degrees. These angles are merely exemplary, and other angles can be used. The sum of these angles can be considered the "coverage" of the sensors on the reference cell 100. In the example of FIG. 2, if angles 240 and 250 are each equal to 30 degrees, then the overall coverage is 60 degrees. The overall coverage can typically be between 45 degrees and 180 degrees. Therefore, in examples where more than three ports are used, the angles between neighboring ports can be smaller.

The spiral grooves 120 on the inner surface of the passageway 110 can be oriented in a direction that either increases or decreases the variation of the fluid mixture that contacts each sensor 212, 222, 232. For example, from the perspective of cross section A-A, spiral grooves 120 that turn in a counter-clockwise direction would reduce the variation of the fluid mixture contacting each sensor 212, 222, 232. This is because the fluid mixture will rotate within the passageway 110, possibly matching the rotational positions of the ports 210, 220, 230. On the other hand, spiral grooves 120 that turn in a clockwise direction would increase the variation of the fluid mixture contacting each sensor 212, 222, 232. In that example, the fluid would rotate in a direction opposite the rotational positions of the ports 210, 220, 230, thereby ensuring that each sensor 212, 222, 232 contacts a different portion of the fluid mixture.

Figure 3:
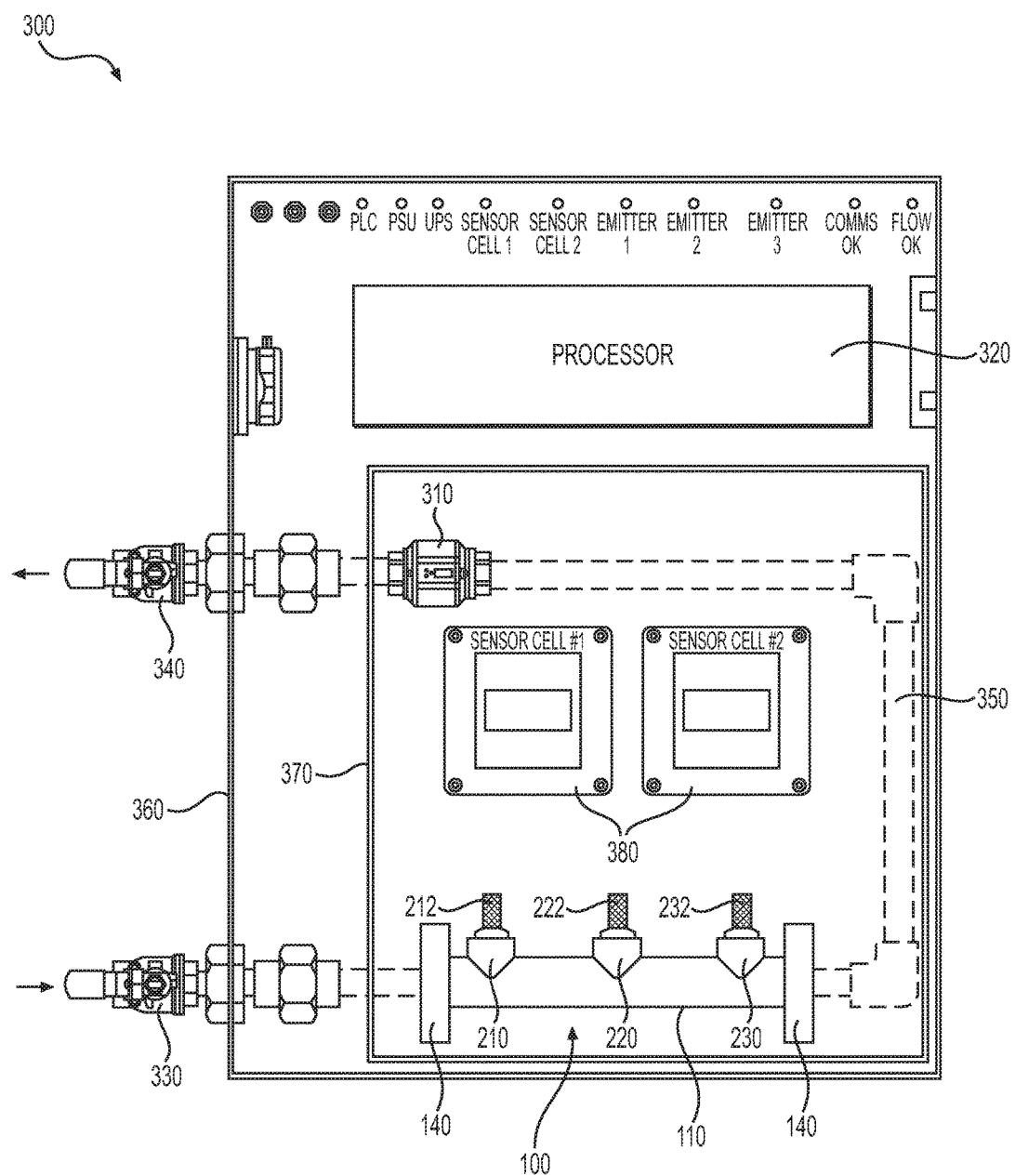
FIG. 3 is an illustration of an example oil-detection unit.

FIG. 3 provides an illustration of an example oil-detection unit 300. The oil-detection unit 300 receives a fluid mixture at an intake valve 330. The intake valve 330 controls the flow rate of the fluid mixture through the reference cell 100. The intake valve 330 can be positioned outside of an outer box 360 of the oil-detection unit 300. As a result, a worker can easily control the flow of the fluid mixture through the oil-detection unit 300 without needing to open or otherwise modify the unit. The fluid mixture entering the intake valve 330 can be received from a three-phase separator or oil-water separator, such as a gun-barrel separator or skimmer, or a combination of these components.

The fluid mixture that enters via the intake valve 330 can travel into the outer box 360 and proceed into the inner box 370 that houses the reference cell 100. As described with respect to FIGS. 1 and 2, the reference cell 100 can include a passageway 110, ports 210, 220, 230, sensors 212, 222, 232, and flanges 140. The fluid mixture than proceeds through a pipe 350 that leads to a flow meter 310. The flow meter 310 measures the flow rate of the fluid mixture through the oil-detection unit 300. The flow meter 310 can measure linear, nonlinear, mass, or volumetric flow rate. In most applications, the flow meter 310 measures a volumetric flow rate of the fluid mixture. The flow meter 310 can also include a temperature sensor that continuously measures the temperature of the fluid mixture. In some examples, the flow meter 310 is placed outside of the inner box 370 but inside the outer box 360. In FIG. 3, the flow meter 310 is located inside the inner box 370 for additional security.

The fluid mixture proceeds from the flow meter 310 to the exit valve 340. After exiting the oil-detection unit 300 via the exit valve 340, the fluid mixture can be discharged, collected for further use, or sent through additional water-purification stages.

The oil-detection unit 300 also includes a processor 320. In practice, the processor 320 can include multiple processors, memory storage devices, and displays. In some examples, the processor 320 is a component of a computing device included in the oil-detection unit 300. In the example of FIG. 3, the processor 320 is located inside the outer box 360 but outside of the inner box 370. In other examples, the processor 320 can be located inside the inner box 370.

The processor 320 can receive information from the sensors 210, 220, 230 as well as the flow meter 310. In some examples, sensor cells 380 are utilized to normalize the amplitude of the signals sent from the sensors 210, 220, 230 and/or flow meter 310 such that the signals are appropriate for the processor 320.

In another example, a second passageway can be installed downstream from passageway 110, such that the fluid mixture passes through the passageway 110 after the second passageway. The second passageway can have a second plurality of sensors in a different orientation than those 212, 222, 232 of the first reference cell 110. This can build additional redundancy in case a sensor 212, 222, 232 goes bad or the orientation of the sensors 212, 222, 232 in the first passageway is not optimal for detecting oil for whatever reason.

The signals received from the sensors 210, 220, 230 and flow meter 310 can be used to calculate a baseline range of values that represents a fluid mixture having less than a threshold proportion of oil. The processor 320 can translate the signals received from the sensors 210, 220, 230 into values corresponding to an amplitude of each signal. In some examples, the values are dimensionless and merely serve as relative measurements over time. The calculation of a baseline range of values can be established via a calibration process performed by the processor 320. Calibration can be performed remotely, automatically, or using a combination of both methods. If an additional passageway with a second plurality of sensors is used, those sensors can also be taken into account in calculating the baseline range and other calculations described herein that involve sensors 212, 222, 232.

For automatic calibration, the processor 320 can monitor signals from the sensors 210, 220, 230 over a period of time where the incoming fluid mixture is known to contain less than the maximum acceptable amount of oil. By comparing the values corresponding to the signals from each sensor 210, 220, 230, the processor 320 can determine a statistical baseline range. The baseline range can be a range of values that bound the fluctuations of the signals from the sensors 210, 220, 230, for example. The baseline range can be recalculated continuously or at predetermined periods of time. For example, the baseline range can be recalculated every second, every 10 seconds, every minute, or any other period of time. Recalculating the baseline range allows for the oil-detection unit 300 to adapt to overall changes to the fluid mixture without producing false positives regarding oil detection.

For remote calibration, a user can provide calibration data to the processor 320. The calibration data can be provided directly, such as through a user interface or buttons associated with the processor 320. In other examples, the calibration data can be provided using an application installed on a remote computing device, such as a smartphone, tablet, or computer. Calibration data can include, for example, an indication that the current fluid mixture contains less than the maximum allowable threshold of oil. Calibration data can also include a starting range of values for the baseline range, which is then recalculated by the processor 320 as described above.

When an influx of oil enters the fluid mixture flowing through the oil-detection unit, the values associated with the signals sent from the sensors 212, 222, 232 can quickly deviate from their previous values. This deviation can cause the values to exceed the baseline range by either dropping below the lower threshold of the baseline range or rising above the upper threshold of the baseline range. Because the deviation occurs quickly, the processor 320 can recognize the deviation before using the deviation to recalculate the baseline range. Because a deviation from the baseline range indicates an event (i.e. an influx of oil in the fluid mixture), the processor 320 seeks to exclude that deviation from the calculation of a baseline range. In some examples, the processor 320 stops recalculating the baseline range when a deviation occurs.

A deviation from the baseline range can occur when two or more sensors 210, 220, 230 deviate from the baseline range. A single sensor 210, 220, or 230 might deviate from the baseline due to a malfunction. Therefore, multiple sensors 210, 220, 230 deviating from the baseline range provides a more accurate indication of oil in the fluid mixture. In an example where only one sensor 210, 220, or 230 deviates from the baseline range, the processor 320 can display a warning on a user interface indicating that the sensor needs to be inspected and either fixed or replaced.

In an example where multiple sensors 210, 220, 230 deviate from the baseline range, the processor 320 can initiate an alarm sequence. The alarm sequence can include, for example, pausing the recalculation of the baseline range. It can also include sending various types of communications to relevant persons or devices. For example, the alarm sequence can include displaying the alarm on a display or user interface associated with the oil-detection unit 300. The alarm sequence can also include sending a message from the processor 320 to an administrator or worker, such as via SMS, MMS, email, instant message, or any other communication method. In some examples, the alarm sequence can include sending a message or instruction to a component upstream of the oil-detection unit 300—for example, to an oil-water separator—indicating the presence of oil downstream from that component. The message can include instructions to alter the treatment of the fluid mixture entering the oil-water separator, for example.

During an alarm sequence, the baseline range can be frozen such that the processor 320 does not recalculate a new baseline range using a fluid mixture with an unacceptable quantity of oil. Instead, the processor 320 can continue monitoring signals from the sensors 210, 220, 230 until those signals return to being within the baseline range. This can happen, for example, after a problem is fixed upstream that reduces the amount of oil in the fluid mixture to an acceptable amount. This could also happen if only a small amount of oil temporarily passed through the oil-detection unit 300. In either case, when the fluid mixture returns to having an acceptably low amount of oil, the values from the sensors 210, 220, 230 can return to the baseline range. At this time, the processor 320 can abate the alarm sequence and continue recalculating the baseline range over time as before. In some examples, the processor 320 can also initiate a communication regarding the oil levels returning to normal, such as by displaying a message on a display or user interface or by sending a message to an administrator or worker.

Figure 4:
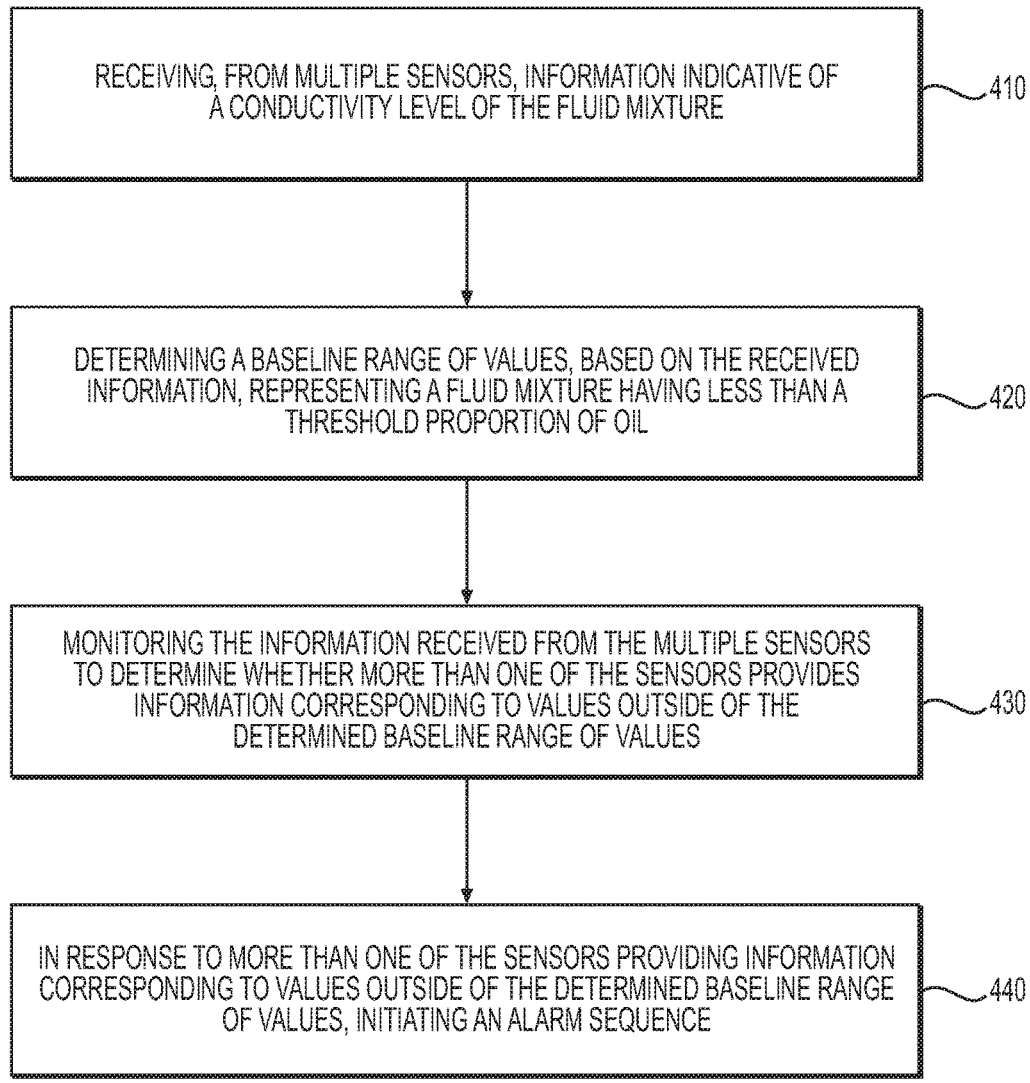
FIG. 4 is a flow chart of an example method for detecting the presence of oil in a fluid mixture.

FIG. 4 is a flow chart of an example method for detecting the presence of oil in a fluid mixture. The stages of the example method can be carried out be a processor 320 executing instructions of a non-transitory, computer-readable medium. At stage 410, the processor 320 can receive, from multiple sensors 210, 220, 230, information indicative of an excitation level of a fluid mixture. This information can be normalized into dimensionless numeric values, for example. The processor 320 can receive a constant stream of information from the sensors 210, 220, 230.

At stage 420, the processor 320 can determine a baseline range of values, based on the received information. The baseline range of values can represent a fluid mixture having less than a threshold proportion of oil. In some examples, the threshold proportion of oil can be programmed by a system administrator. In other examples, the threshold proportion of oil can be manually entered by a user. The determination of the baseline range can be done using statistical analysis techniques known in the art.

At stage 430, the processor 320 can monitor the information received from the multiple sensors to determine whether more than one of the sensors provides information corresponding to values outside of the determined baseline range of values. For example, the processor 320 can establish an upper and lower limit for the baseline range of values, and determine that the signals from more than one sensor correspond to values that are either above the upper limit or below the lower limit for the baseline range.

At stage 440, in response to more than one of the sensors providing information corresponding to values outside of the determined baseline range of values, the processor 320 can initiate an alarm sequence. The alarm sequence can include, for example, pausing the recalculation of the baseline range. It can also include sending various types of communications to relevant persons or devices. For example, the alarm sequence can include displaying the alarm on a display or user interface associated with the oil-detection unit 300. The alarm sequence can also include sending a message from the processor 320 to an administrator or worker, such as via SMS, MMS, email, instant message, or any other communication method. In some examples, the alarm sequence can include sending a message or instruction to a component upstream of the oil-detection unit 300—for example, to an oil-water separator—indicating the presence of oil downstream from that component. The message can include instructions to alter the treatment of the fluid mixture entering the oil-water separator, for example.

During an alarm sequence, the baseline range can be frozen such that the processor 320 does not recalculate a new baseline range using a fluid mixture with an unacceptable quantity of oil. Instead, the processor 320 can continue monitoring signals from the sensors 210, 220, 230 until those signals return to being within the baseline range. This can happen, for example, after a problem is fixed upstream that reduces the amount of oil in the fluid mixture to an acceptable amount. This could also happen if only a small amount of oil temporarily passed through the oil-detection unit 300. In either case, when the fluid mixture returns to having an acceptably low amount of oil, the values from the sensors 210, 220, 230 can return to the baseline range. At this time, the processor 320 can abate the alarm sequence and continue recalculating the baseline range over time as before. In some examples, the processor 320 can also initiate a communication regarding the oil levels returning to normal, such as by displaying a message on a display or user interface or by sending a message to an administrator or worker.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An oil-detection unit for detecting the presence of oil in a fluid mixture, comprising:
   a reference cell having a passageway for channeling the fluid mixture and a plurality of ports coupled to the passageway;
   a plurality of sensors, each sensor positioned at least partially within one of the plurality of ports, wherein each of the plurality of sensors produces a signal indicative of the excitation of the fluid mixture flowing through the reference cell;
   a flow meter that measures the flow rate of the fluid mixture through the reference cell; and a processor that:
  receives signals from each of the plurality of sensors and the flow meter;
  determines, based on the received signals, whether the fluid mixture contains at least a threshold amount of oil; and
  based on a determination that the fluid mixture contains at least the threshold amount of oil, initiates an alarm.

2. The oil-detection unit of claim 1, wherein the passageway of the reference cell has an inner surface comprising a plurality of spiral grooves.

3. The oil-detection unit of claim 1, wherein at least two of the plurality of ports are oriented such that their respective central axes form at least a 10-degree angle, relative to one another, when viewed from a perspective aligned with the overall direction of fluid flow through the reference cell.

4. The oil-detection unit of claim 1, wherein initiating an alarm further comprises sending an electronic notification to a user.

5. The oil-detection unit of claim 4, further comprising a second passageway with a second plurality of sensors within the reference cell, the second plurality of sensors being oriented differently than those of the first passageway, and wherein the processor receives additional signals from of the second plurality of sensors that are used in the determination.

6. The oil-detection unit of claim 1, wherein the processor determines whether the fluid mixture contains at least a threshold amount of oil by establishing a baseline range of values received from the plurality of sensors, and comparing the output from the plurality of sensors to the established baseline range.

7. The oil-detection unit of claim 6, wherein the processor recalculates the baseline range of values received from the plurality of sensors after a predetermined period of time.

8. A reference cell for detecting the presence of oil in a fluid mixture, comprising:
  a passageway for channeling a fluid mixture, the passageway having an inner surface, an entrance for receiving the fluid mixture, and an exit for expelling the fluid mixture, wherein the inner surface of the passageway comprises a plurality of spiral grooves; and
  a plurality of ports coupled to the passageway and oriented such that a central axis of each of the plurality of ports perpendicularly intersects a longitudinal axis of the passageway,
  wherein each of the plurality of ports is shaped to house a sensor for detecting oil in a fluid mixture, and
  wherein at least two of the ports are oriented such that their respective central axes form at least a 10-degree angle when viewed from a perspective aligned with the direction of the longitudinal axis of the passageway.

9. The reference cell of claim 8, comprising three ports, wherein each port is offset at least 10 degrees relative to the other two ports, when viewed from a perspective aligned with the direction of the longitudinal axis of the passageway.

10. The reference cell of claim 8, comprising three ports, wherein each port is offset at least 20 degrees relative to the other two ports, when viewed from a perspective aligned with the direction of the longitudinal axis of the passageway.

11. The reference cell of claim 8, further comprising a plurality of sensors shaped to fit at least partially within the plurality of ports, respectively.

12. The reference cell of claim 11, wherein the sensors are electrical sensors.

13. The reference cell of claim 8, wherein the plurality of ports span at least 40 degrees, when viewed from a perspective aligned with the direction of the longitudinal axis of the passageway.

14. The reference cell of claim 8, further comprising a first flange coupled to the passageway and located proximate the entrance of the passageway, and a second flange coupled to the passageway and located proximate the exit of the passageway, the first and second flanges each having at least two apertures for receiving fasteners.

15. A non-transitory, computer-readable medium containing instructions that, when executed by a processor, performs stages for detecting the presence of oil in a fluid mixture, the stages comprising:
  receiving information from a plurality of sensors, said information indicative of a excitation level of the fluid mixture;
  determining a baseline range of values, based on the received information, wherein the baseline range of values represents a fluid mixture having less than a threshold proportion of oil;
  monitoring the information received from the plurality of sensors to determine whether more than one of the plurality of sensors provide information corresponding to values outside of the determined baseline range of values; and
  in response to more than one of the plurality of sensors providing information corresponding to values outside of the determined baseline range of values, initiating an alarm sequence.

16. The non-transitory, computer-readable medium of claim 15, wherein the alarm sequence comprises sending a notification to a user.

17. The non-transitory, computer-readable medium of claim 15, wherein determining a baseline range of values includes recalculating the baseline range of values after a predetermined period of time.

18. The non-transitory, computer-readable medium of claim 17, wherein the alarm sequence causes the processor to stop recalculating the baseline range of values.

19. The non-transitory, computer-readable medium of claim 18, wherein recalculating the baseline range of values continues after the alarm sequence has abated.

20. The non-transitory, computer-readable medium of claim 19, wherein the alarm sequence is abated when the information from the plurality of sensors corresponds to values within the determined baseline range of values.

* * * * *